United States Patent [19]

Lindel et al.

[11] Patent Number: 4,895,950
[45] Date of Patent: Jan. 23, 1990

[54] 5-HALOGENO-6-AMINO-NICOTINIC ACID HALIDES

[75] Inventors: Hans Lindel, Leverkusen; Werner Hallenbach, Langenfeld, both of Fed. Rep. of Germany

[73] Assignee: Bayer Aktiengesellschaft, Leverkusen, Fed. Rep. of Germany

[21] Appl. No.: 216,047

[22] Filed: Jul. 7, 1988

[30] Foreign Application Priority Data

Jul. 11, 1987 [DE] Fed. Rep. of Germany ....... 3723069

[51] Int. Cl.⁴ .................. C07D 213/72; C07D 213/75; C07D 213/78; C07D 213/81
[52] U.S. Cl. .................................... 546/309; 546/193; 546/282; 546/310; 544/131
[58] Field of Search ................ 546/309, 310

[56] References Cited

U.S. PATENT DOCUMENTS 4,129,734 12/1978 McKendry .......................... 546/309
4,596,883 6/1986 Schwindeman et al. ........... 546/309

FOREIGN PATENT DOCUMENTS 0244728 11/1987 European Pat. Off. ............ 546/309
2419535 12/1974 Fed. Rep. of Germany ...... 546/309

OTHER PUBLICATIONS

Patent Abstracts of Japan, vol. 10, No. 239, Aug. 19, 1986.
Houben-Weyl Methoden der Organischen Chemie, vol. VII/2b, 1976, pp. 1339–1346.
Houben-Weyl Methoden der Organischen Chemie, vol. VII/2a, 1973, pp. 520–522.

Primary Examiner—Mary C. Lee
Assistant Examiner—Johann Richter
Attorney, Agent, or Firm—Sprung, Horn, Kramer & Woods

[57] ABSTRACT

Novel 5-halogeno-6-amino-nicotinic acid halides of the formula

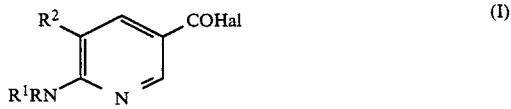

in which
R represents hydrogen or alkyl,
$R^1$ represents hydrogen, alkyl or acyl or
R and $R^1$, together with the nitrogen atom to which they are bonded, represent an optionally substituted heterocyclic radical,
$R^2$ represents halogen and
Hal represents halogen, are prepared by halogenating the corresponding nicotinic acids. The Co Hal moiety is converted to $CH_3$ by reaction with $$R^3OMgCR^4(COOR^3)_2 \qquad (IV)$$

in which
$R^3$ represents $C_{1-3}$ alkyl and
$R^4$ represents hydrogen or $C_1$–$C_2$-alkyl, and then hydrolyzing and decarboxylating the product.

7 Claims, No Drawings

5-HALOGENO-6-AMINO-NICOTINIC ACID HALIDES

The present invention relates to new 5-halogeno-6-amino-nicotinic acid halides, processes for their preparation and their use for the preparation of the corresponding 3-pyridylalkyl ketones.

3-Pyridylalkyl ketones are useful intermediate products for the preparation of growth-promoting pyridylethanolamines. The ketones and their preparation are described generally in Application Serial No. 40,509, filed Apr. 20, 1987, now pending, corresponding to German Patent Application P 36 15 293.5. They are obtained by the processes described therein, by a procedure in which nicotinic acid alkyl esters are reacted with acetic acid alkyl esters in a Claisen ester condensation and the pyridoylacetic acid esters thus obtained are hydrolyzed and decarboxylated.

The following have now been found:

1. 5-Halogeno-6-amino-nicotinic acid halides of the formula (I)

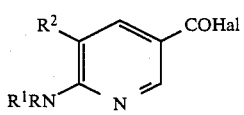

in which
R represents hydrogen or alkyl,
$R^1$ represents hydrogen, alkyl or acyl or
R and $R^1$, together with the nitrogen atom to which they are bonded, represent an optionally substituted heterocyclic radical,
$R^2$ represents halogen and
Hal represents halogen.

2. Process for the preparation of the 5-halogeno-6-amino-nicotinic acid halides of the formula (I)

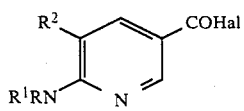

in which
R represents hydrogen or alkyl,
$R^1$ represents hydrogen, alkyl or acyl or
R and $R^1$, together with the nitrogen atom to which they are bonded, represent an optionally substituted heterocyclic radical,
$R^2$ represents halogen and
Hal represents halogen.
characterized in that 5-halogeno-6-amino-nicotinic acids of the formula (II)

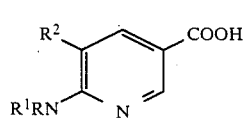

in which
R, $R^1$ and $R^2$ have the abovementioned meaning, are halogenated.

3. Use of 5-halogeno-6-amino-nicotinic acid halides of the formula (I)

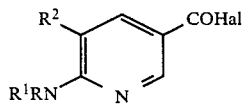

in which
R represents hydrogen or alkyl,
$R^1$ represents hydrogen, alkyl or acyl or
R and $R^1$, together with the nitrogen atom to which they are bonded, represent an optionally substituted heterocyclic radical,
$R^2$ represents halogen and
Hal represents halogen,
for the preparation of 5-acetylpyridines of the formula (III)

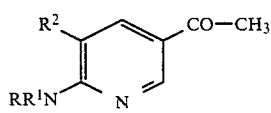

in which
R, $R^1$ and $R^2$ have the abovementioned meaning, characterized in that 5-halogeno-6-amino-nicotinic acid halides of the formula (I) are reacted with a compound of the formula (IV)

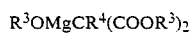

$$R^3OMgCR^4(COOR^3)_2 \qquad (IV)$$

in which
$R^3$ represents $C_{1-3}$ alkyl and
$R^4$ represents hydrogen or $C_1$–$C_2$-alkyl,
and the products are then hydrolyzed and decarboxylated.

The 3-pyridylalkyl ketones and, from these, the pyridylethanolamines are available in good yields and starting from inexpensive starting products with the aid of the 5-halogeno-6-amino-nicotinic acid halides according to the invention.

Preferred compounds of the formula (I) are those in which
$R^2$ represents chlorine or bromine,
R represents hydrogen or $C_1$–$C_3$-alkyl,
$R^1$ represents hydrogen, $C_1$–$C_3$-alkyl or $C_1$–$C_3$-alkanoyl, or
R and $R^1$, together with the nitrogen atom to which they are bonded, represent a heterocyclic radical and
Hal represents chlorine or bromine.

Particularly preferred compounds of the formula (I) are those
in which
$R^2$ represents chlorine or bromine,
Hal represents chlorine,
R represents hydrogen or methyl and
$R^1$ represents hydrogen, methyl or acetyl, or
R and $R^1$, together with the nitrogen atom to which they are bonded, represent a 5- or 6-membered ring, such as pyrrolidinyl, pyrryl, piperidinyl or morpholinyl.

The following compounds of the formula (I) may be mentioned specifically: 5-bromo-6-aminonicotinoyl chloride, 5-chloro-6-aminonicotinoyl chloride, 5-bromo-6-methylaminonicotinoyl chloride, 5-chloro-6-acetaminonicotinoyl chloride, 5-bromo-6-N-pyrrolidino-nicotinoyl chloride and 5-chloro-6-N-morpholino-nicotinoyl chloride.

If, in process (2), 5-bromo-6-methylaminonicotinic acid is used as the 5-halogeno-6-aminonicotinic acid of the formula (II) and thionyl chloride is used as the halogenating agent, the reaction can be represented by the following equation:

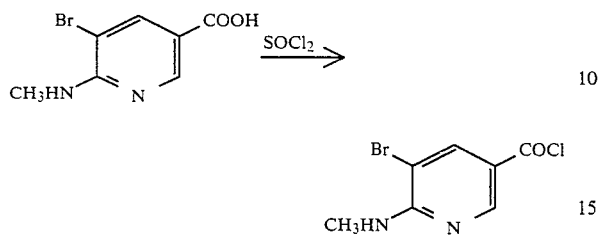

The compounds of the formula (II) are known in some cases or they can be prepared by processes analogous to known processes (Graf, J. prakt. Chem. (2) 138 (1933) page 244). Preferred compounds of the formula (II) are those in which R, $R^1$ and $R^2$ have the meanings given in the case of the compounds of the formula (I).

The following compounds of the formula (II) may be mentioned specifically: 5-bromo-6-aminonicotinic acid, 5-chloro-6-aminonicotinic acid, 5-bromo-6-methylaminonicotinic acid, 5-chloro-6-acetaminonicotinic acid, 5-bromo-6-N-pyrrolidino-nicotinic acid and 5-chloro-6-N-morpholino-nicotinic acid.

Inorganic acid chlorides are used as the halogenating agents. Examples which may be mentioned are: phosphorus oxychloride, phosphorus pentachloride and thionyl chloride.

The reaction is carried out by treating a compound of the formula (II) with 1 to 1.5 equivalents of the inorganic acid chloride, if appropriate in a diluent.

The reaction is carried out at temperatures from 20° C. to 150° C., preferably under normal pressure.

Diluents which can be used are all the inert organic solvents. These include, in particular, aliphatic and aromatic optionally halogenated hydrocarbons, such as pentane, hexane, cyclohexane, benzene, toluene, methylene chloride, chloroform and chlorobenzene; ethers, such as diethyl ether, tetrahydrofuran and dioxane, and phosphorus oxychloride.

If, in process (3), 5-bromo-6-N-pyrrolonicotinoyl chloride is used as the compound of the formula (I) and dimethyl methoxymagnesium-malonate is used as the compound of the formula (IV), process (3) can be represented by the following equation:

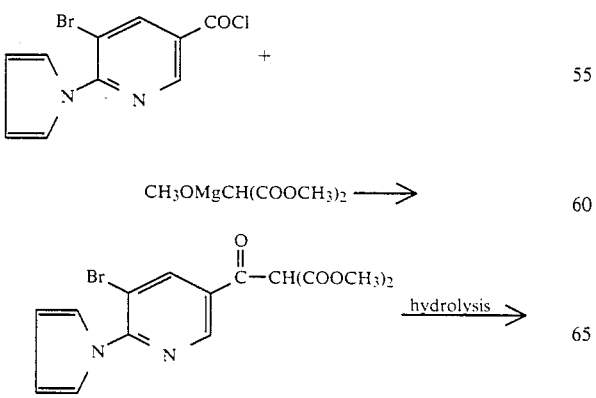

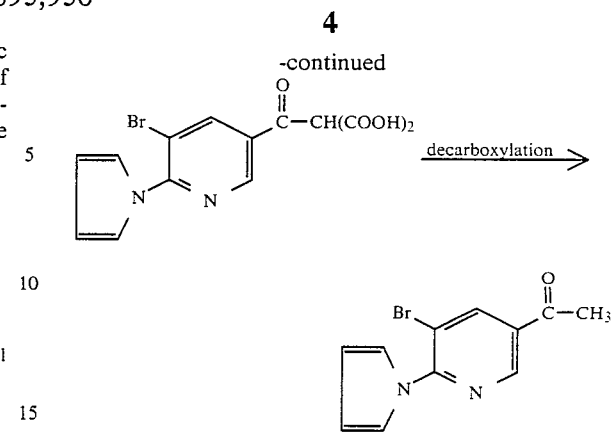

Compounds of the formula (IV) are known (Org. Synth. Coll. Vol. IV (1963), 285; and Ber. dt. Chem. Ges. 67 (1934), 935).

The following compounds of the formula (IV) may be mentioned specifically: dimethyl methoxymagnesium-malonate, diethyl ethoxymagnesiummalonate and diethyl ethoxymagnesiummethylmalonate.

Process (3) is carried out by reacting equimolar amounts of the compounds of the formulae (I) and (IV) in a diluent and then hydrolyzing the product, the β-keto-dicarboxylic acid being decarboxylated. Diluents used are all the inert organic solvents. These include optionally halogenated aliphatic and aromatic hydrocarbons, such as pentane, hexane, benzene, toluene, methylene chloride, chloroform and chlorobenzene; ethers, such as diethyl ether and tetrahydrofurane and alcohols, such as methanol and ethanol. The reaction is carried out at temperatures from 20° C. to 150° C., preferably at the boiling point of the solvent used.

The hydrolysis is carried out with inorganic acids, such as hydrochloric acid or sulphuric acid, or organic carboxylic acids, such as acetic acid or propionic acid. It is also possible to use mixtures of inorganic and organic acids. The hydrolysis can also be carried out with bases, such as alcoholic or aqueous solutions of alkali and alkaline earth metal hydroxides or carbonates, for example sodium, potassium or barium hydroxide or sodium or potassium carbonate.

The 2-amino-3-halogeno-5-acetylpyridines obtainable by process (3) according to the invention are used for the preparation of pyridine-ethanolamine derivatives. For this, the acetylpyridines are reacted with elemental halogen or with copper halides. The halogenomethylpyridyl ketones thereby obtainable are then reacted with amines and the pyridyl-aminomethyl ketones thereby obtained are reduced. This reaction can be illustrated by the following equation:

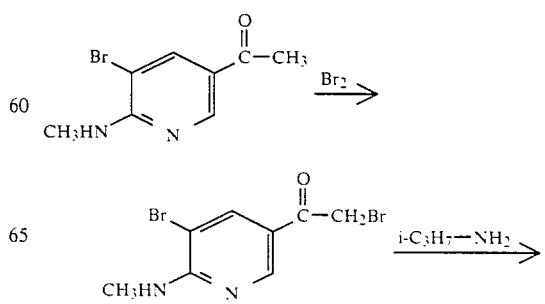

-continued

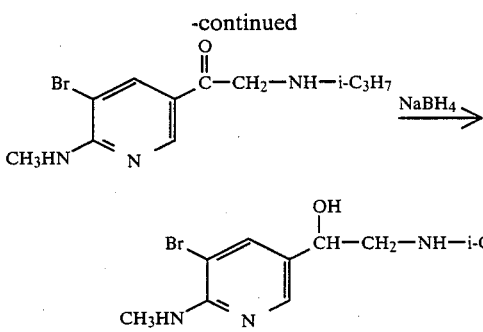

The halogenomethylpyridyl ketones can also first be reduced to the pyridylhalogenoethanols and these can then be reacted with amines to give pyridylethanolamines.

The procedure for these reactions is described in Application Serial No. 40,509, supra.

PREPARATION EXAMPLES

Example of process (2) 5-Chloro-6-amino-nicotinoyl chloride 6.3 g (36 mmol) of 5-chloro-6-amino-nicotinic acid are heated under reflux in 60 ml of thionyl chloride for 4 hours. After the volatile constituents have been distilled off, 50 ml of toluene are added to the residue and the mixture is evaporated. 6.9 g of 5-chloro-6-amino-nicotinoyl chloride are obtained as crystals of melting point: >250° C.

Example of process (3) 2-Amino-3-chloro-5-acetylpyridine 7.2 g (37.5 mmol) of 5-chloro-6-aminonicotinoyl chloride in 10 ml of absolute tetrahydrofuran are added to a boiling solution of 8.55 g (37.5 mmol) of diethyl ethoxymagnesium-malonate (prepared in accordance with Org. Synth. Coll. Vol. IV (1963), 285) in 120 ml of absolute tetrahydrofuran and the mixture is heated under reflux for 2 hours. After neutralization with 2N sulphuric acid, the organic phase is separated off and evaporated. The residue is heated under reflux in a mixture of 30 ml of glacial acetic acid, 20 ml of water and 5 ml of concentrated sulphuric acid for 4 hours. The mixture is stirred into ice-water, brought to pH 4 and extracted with ethyl acetate. Drying and evaporation gives 5.4 g (85%) of the title compound, melting point: 188° C.

EXAMPLE OF THE PREPARATION OF THE HALOGENOMETHYLPYRIDYL KETONES

Example a

2-Amino-3-chloro-5-pyridyl bromomethyl ketone 16 g (0.1 mol) of bromine are added dropwise to a solution of 17.0 g (0.1 mol) of 2-amino-3-chloro-5-acetylpyridine in a mixture of 19.3 g of hydrogen bromide (47% strength aqueous solution; 0.11 mol) and 500 ml of glacial acetic acid. The mixture is subsequently stirred for two hours, brought to pH 8 and extracted with ethyl acetate. Drying and evaporation gives 18.5 g (74%) of the title compound, melting point 134° C. Example of the preparation of the pyridyl-aminomethyl ketones Example 6

2-Amino-3-chloro-5-pyridyl isopropylaminomethyl ketone 9.98 g (0.04 mol) of the compound prepared according to Example a are introduced in portions into a solution of 11.8 g (0.2 mol) of isopropylamine in 150 ml methanol at 0° C. The mixture is allowed to come to room temperature and is subsequently stirred for two hours and evaporated. The residue is taken up in buffer to pH 5 and the mixture is washed with ether. The aqueous phase is brought to pH 9 and extracted with ethyl acetate. After drying and evaporation, 6.8 g (75%) of the title compound are obtained as an amorphous powder. Example of the preparation of the pyridylethanolamines Example c 1-(2-Amino-3-chloro-5-pyridyl)-2-isopropylaminoethanol 0.38 g (10 mmol) of sodium borohydride is added in portions to a solution of 2.28 g (10 mmol) of the compound prepared according to Example b in 50 ml of methanol at 0° C. The mixture is allowed to come to room temperature and is brought to pH 1 with dilute hydrochloric acid and evaporated. The residue is taken up in water and the mixture is washed with ether. It is then brought to pH 10 and extracted with ethyl acetate. Drying and evaporation gives 2.1 g (92%) of the title compound, melting point 146° C.

It will be appreciated that the instant specification and claims are set forth by way of illustration and not limitation, and that various modifications and changes may be made without departing from the spirit and scope of the present invention.

What is claimed is:

1. A 5-halogeno-6-amino-nicotinic acid halide of the formula

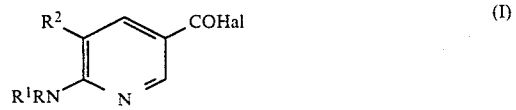

(I)

in which
R represents hydrogen or alkyl,
$R^1$ represents hydrogen, alkyl or acyl,
$R^2$ represents halogen and
Hal represents halogen.

2. A 5-halogeno-6-amino-nicotinic acid halide according to claim 1, in which
$R^2$ represents chlorine or bromine,
R represents hydrogen or $C_1$–$C_3$-alkyl,
$R^1$ represents hydrogen, $C_1$–$C_3$-alkyl or $C_1$–$C_3$-alkanoyl, and
Hal represents chlorine or bromine.

3. A 5-halogeno-6-amino-nicotinic acid halide according to claim 1, in which
$R^2$ represents chlorine or bromine,
Hal represents chlorine,
R represents hydrogen or methyl and
$R^1$ represents hydrogen, methyl or acetyl.

4. A compound according to claim 1, wherein such compound is 5-bromo-6-aminonicotinoyl chloride.

5. A compound according to claim 1, wherein such compound is 5-chloro-6-aminonicotinoyl chloride.

6. A compound according to claim 1, wherein such compound is 5-bromo-6-methylaminonicotinoyl chloride.

7. A compound according to claim 1, wherein such compound is 5-chloro-6-acetaminonicotinoyl chloride.

* * * * *